United States Patent
Maschke

(10) Patent No.: US 7,650,888 B2
(45) Date of Patent: Jan. 26, 2010

(54) METHOD AND SYSTEM FOR IDENTIFICATION OF A MEDICAL IMPLANT

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 321 days.

(21) Appl. No.: 11/709,661

(22) Filed: Feb. 22, 2007

(65) Prior Publication Data

US 2007/0232884 A1 Oct. 4, 2007

(30) Foreign Application Priority Data

Feb. 22, 2006 (DE) .............. 10 2006 008 258

(51) Int. Cl.
*A61B 19/00* (2006.01)

(52) U.S. Cl. .............. 128/899; 340/539.12; 607/60

(58) Field of Classification Search .............. 128/899; 340/572.1, 572.8, 573.1, 539.12; 600/300; 235/375, 376, 385, 492

See application file for complete search history.

(56) References Cited

U.S. PATENT DOCUMENTS

| 6,185,452 | B1 | 2/2001 | Schulman et al. |
| 6,239,724 | B1 | 5/2001 | Doron et al. |
| 6,878,112 | B2 | 4/2005 | Linberg et al. |
| 7,218,232 | B2 * | 5/2007 | DiSilvestro et al. ...... 340/572.8 |
| 7,333,013 | B2 * | 2/2008 | Berger .............. 340/539.12 |
| 7,474,223 | B2 * | 1/2009 | Nycz et al. .............. 340/572.8 |
| 2001/0037220 | A1 | 11/2001 | Merry et al. |
| 2001/0049544 | A1 | 12/2001 | Lee |
| 2006/0031378 | A1 | 2/2006 | Vallapureddy et al. |
| 2006/0212096 | A1 * | 9/2006 | Stevenson .............. 607/60 |
| 2006/0235488 | A1 * | 10/2006 | Nycz et al. .............. 607/60 |
| 2007/0239481 | A1 * | 10/2007 | DiSilvestro et al. .......... 705/2 |

FOREIGN PATENT DOCUMENTS

| WO | WO 01/47410 A2 | 7/2001 |
| WO | WO 2004/039256 A2 | 5/2004 |

* cited by examiner

*Primary Examiner*—John P Lacyk

(57) ABSTRACT

The invention relates to a method and a system for identification of a medical implant that is inserted into a patient. Identification data of the medical implant is stored in an RFID chip. The RFID chip is inserted into the body of the patient. The RFID chip can be inserted into a different location than the medical implant into the body of the patient or can be arranged on the medical implant. A signal from the RFID chip comprising the identification data of the medical implant is called up by a reading unit.

9 Claims, 1 Drawing Sheet

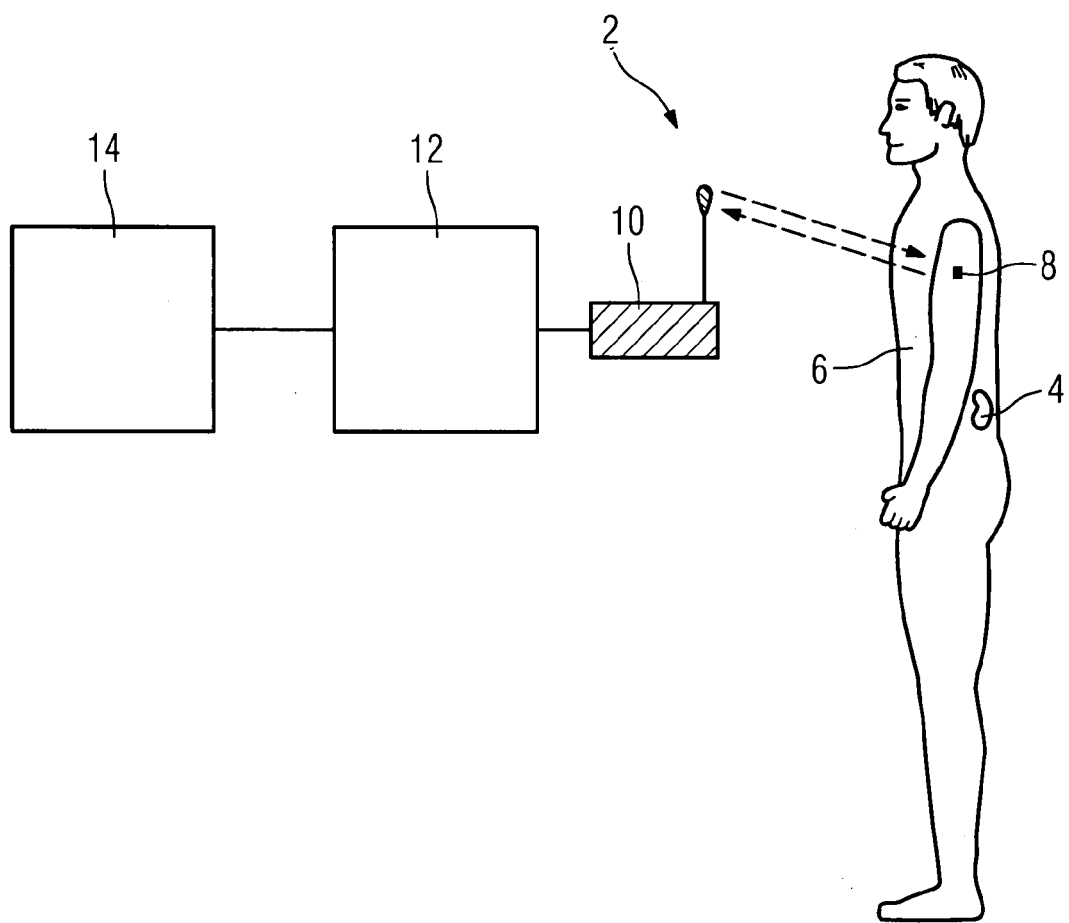

METHOD AND SYSTEM FOR IDENTIFICATION OF A MEDICAL IMPLANT

CROSS REFERENCE TO RELATED APPLICATIONS

This application claims priority of German application No. 10 2006 008 258.3 filed Feb. 22, 2006, which is incorporated by reference herein in its entirety.

FIELD OF THE INVENTION

The invention relates to a method and a system for identification of a medical implant in a patient.

BACKGROUND OF THE INVENTION

Medical implants are used in various illnesses to support or replace organs, tissue or vessels. Information on the implant in use is usually entered in the patient's records in the hospital by medical personnel, in order to record a timepoint, method and type of implant.

The disadvantage of this procedure is that the patient's record is archived in the hospital that carried out the implant. The patient usually has no complete information regarding the inserted implant. In an emergency or during a visit to a different doctor or different clinic, the patient's record with the information on the implant must first be requested. Sometimes the patient has forgotten whether he is carrying an implant or is unconscious after an accident and cannot tell the medical personnel that he is carrying an implant. If it is a metal implant, this can be dangerous for the patient if, for example, he is being subjected to an examination using a magnetic resonance system. Because of the above disadvantages, it is therefore usually necessary to examine the patient using an imaging process such as X-ray, CT or ultrasound to determine whether he is carrying an implant. However, this imaging procedure provides no detailed information, e.g. regarding the date of the implantation or the serial number of the implant.

SUMMARY OF THE INVENTION

The object of this invention is to enable an implant inserted in a patient to be quickly detected and all the necessary information regarding the implant to be obtained.

The object is achieved by a method as claimed in the claims. According to this, data and information regarding the implant, carried on an RFID chip in the body of the patient, is read with the aid of a reading device.

Radio frequency identification (RFID) is a method by means of which a radio frequency with a low transmission power is used for the contactless transmission of data. An RFID system generally includes a transponder (RFID chip, antenna and, if necessary, an energy source) and a reading unit that is especially connected to a computer-aided evaluation module. RFID chips can have a multiwriteable memory in which information is stored. The RFID transponder must be supplied with energy to enable information to be read or saved.

A distinction is made between two types of RFID transponder, depending on the energy supply. Passive RFID transponders function without an own energy source and obtain their energy from the radio waves transmitted by the reading unit when the chip is within the reading range of the reading unit. Passive RFID transponders are often designed as read-only chips that cannot be modified. This guarantees a high degree of data security. Alternatively, they can however also have multiwriteable chips. Passive RFID transponders are small and inexpensive. As an alternative to the passive transponders, there are also active RFID transponders that have a built-in energy source, especially a battery. The active RFID transponders are multiwriteable and have a greater signal range and memory capacity than the passive RFID transponders. The active RFID transponders are, of course, somewhat larger and more expensive. The type of transponder used to identify an implant depends upon the application, the size and the memory requirements.

The main advantage in using an RFID chip to identify an implant is that it enables all the necessary data on the implant to be safely and reliably stored, and output as required. Complete and accurate information on the medical implant is called up as required without patients themselves having to provide this information or a patient's record having to be requested. This also avoids expensive, time-consuming examinations that lead to delays in treatment and sometimes can be decisive for the successful outcome of the treatment. The RFID technology also enables defective implants to be more easily identified in the event of a recall action. A further advantage is the facility to identify reused implants in clinics, for example after reprocessing.

Medical implants in this case include implants that are used to improve the health of the patient and also those used for aesthetic reasons. The information stored in the chip can, for example, be data such as the type of implant, the manufacturer, the date of manufacture, brand, type, serial number, dimensions, service life and date of implantation (month, year). The date of the last medical examination can also be entered if it is a writeable chip. Furthermore, writeable chips can be used to store information on implants already present in the body of the patient or to be implanted later. A particular advantage of this embodiment is that only one RFID chip is used to contain the information on all the implants inserted in the body of the patient.

According to a preferred variant, the RFID chip is arranged at a location other than that of the implant. A decisive advantage of this variant is that implants can be identified that are approximately the size of the chip or even smaller, e.g. a stent for supporting blood vessels. This variant is also particularly advantageous for identifying metal implants that otherwise if close to the transponder would disturb the radio signal. The chip can, for example, be inserted directly under the skin of the patient, especially in the area of the upper arm. This also enables the chip to be quickly and easily replaced, e.g. after its service life has elapsed or if faults occur etc.

According to a further preferred variant, the RFID chip is used to identify biological implants. The term biological implants includes those types of organs, tissue, vessels and stem cells that can be implanted in a patient for medical or aesthetic reasons. An identification of this kind is particularly easy to implement in combination with a variant where the RFID chip is disposed at a site other than that of the implant. A separately located chip can be quickly and easily inserted without this having a negative effect on the susceptibility of the body of the patient to the biological implant. In particular, the RFID chip can be inserted in a separate step when the body of the patient has accepted the implant.

In addition to biological and artificial permanent implants, auxiliary medical instruments and temporary implants that are removed after a certain time are often used. Such temporary implants are, for example, screws for fixing bones. There are also a number of surgical instruments that are used when operating on the body of a patient, such as temporary heart pacemaker electrodes, catheters, guidewires, operating clamps etc. A temporary implant or a medical instrument is preferred as the implant for this reason. The advantage of identifying the medical instrument by means of an RFID transponder is that it precludes the possibility of surgical instruments and temporary implants being left forgotten in the body of the patient during an operation. For this purpose, the temporary implants and instruments are identified and recorded by a reading unit in the treatment room before the medical intervention. Therefore, it is easy to check after the operation that all temporary implants and instruments have been removed from the patient.

To further facilitate the diagnosis and treatment of patients, data on the patient is preferably stored in the RFID chip. Examples of patient-specific data are the exact date of the implantation, the name of the patient, the date of birth of the patient and his blood group.

As an alternative to a separate location of the implant and RFID chip, the RFID chip is fitted to the implant. The advantage of this is that only one operative step is required to both fit the implant and the chip at the same location.

It is useful if the identification of the implant is used to determine the position of the patient. The application of the RFID technology is thus expanded in that not only is the implant identified but the location of the patient is also established. This can advantageously avoid the patient being in the vicinity of an electromagnetic field that would disturb his metal implant or heart pacemaker. It can also enable a missing patient to be located within the hospital.

In order not to endanger the health of a patient, the medical implant is identified before performing a medical examination and/or treatment. This enables a timely determination of the presence of an implant so that examinations and treatment that could impair the implant or the wellbeing of the patient are avoided.

In a preferred variant of the embodiment, the RFID chip is supplied with energy by radio waves from the reading unit. This corresponds to a passive RFID transponder. The advantage of this is that by doing away with an internal energy source, such as a battery, the dimensions of the chip can be kept particularly small. Furthermore, the service life of the passive RFID chip is significantly longer than if an active RFID transponder is used because there is no need to replace it due to an exhausted battery.

The use of the RFID technology to mark or identify implants is not limited to the field of the medical care of humans. In a wider sense, patient in this case not only includes human patients but also animal patients. Accordingly, RFID chips are preferably also fitted to animals. This particularly improves the medical care of domestic animals. Further to this, the RFID identification can be used with laboratory animals to aid research.

The object is further achieved by the invention by a system for identification of a medical implant of a patient, including an RFID chip on which implant-specific information is stored and a reading unit contained in an evaluation module. The advantages given with respect to the method and the preferred embodiment variants are to be transferred as appropriate to this system.

With this system, the RFID chip is advantageously located separate from the implant. It is furthermore advantageous if the evaluation module is a medical examination device, especially an X-ray system. In this case the implant is preferably formed from the following group: biological implant, temporary implant, medical instrument.

BRIEF DESCRIPTION OF THE DRAWINGS

An exemplary embodiment of the invention is explained in more detail with the aid of a drawing. In this, the single illustration is a clear schematic and simple representation of a system for the identification of medical implants in a patient.

DETAILED DESCRIPTION OF THE INVENTION

The illustration shows a system 2 for identification of medical implants 4 that essentially include an RFID chip 8 and a reading unit 10 inserted in the body of a patient 6. The reading unit 10 is part of a computer-aided evaluation module 12 or is connected with same. The evaluation module 12 is, in particular, an imaging examination device, e.g. an X-ray system fitted with an RFID reading unit 10. When the reading unit 10 receives information on the implant, the data can be used to optimize the settings of the X-ray system 12 to take account of the implant.

In this exemplary embodiment, the evaluation module 12 is also connected to an information system 14 of the hospital. An electronic record of the patient can thus be automatically called up or created in which data, e.g. regarding the examination, treatment or condition of the patient are stored or are being stored. If the RFID chip 8 is a writeable chip, the information from the information system 14 can be used to activate the reading unit 10 and store new data on the chip 8. To increase the data security for a writeable chip 8, authentication and encryption algorithms are used in the evaluation module 12.

In this exemplary embodiment, the implant 4 is a biological implant, a kidney, that has been transplanted to the patient. In this case, the RFID chip 8 is not fitted directly to the kidney 4 or in the area of the kidney 4 but instead in the upper arm of the patient 6, under his skin. The advantage of this is that the insertion of the chip 8 is easier and quicker, without a major surgical intervention being necessary. Furthermore, the chip 8 was inserted at a later timepoint than the kidney transplant, so that the immune system of the patient 6 was not stressed by two foreign bodies at the same time.

The RFID chip 8 has no energy source of its own and is supplied with energy only in a reading range of the reading unit 10 by the received radio waves of the reading unit 10.

The RFID chip 8 in this exemplary embodiment contains information on the type of transplanted organ, the date of transplantation, the name of the hospital in which the transplantation was performed, the date of birth of the patient and his blood group.

The invention claimed is:

1. A method for identifying a medical implant inserted into a patient, comprising:
   storing an identification data of the implant in an RFID chip;
   inserting the RFID chip into a body of the patient that is different than a location of the implant; and
   receiving a signal from the RFID chip comprising the identification data of the implant by a reading unit.

2. The method as claimed in claim 1, wherein the RFID chip is inserted under a skin of the patient.

3. The method as claimed in claim 2, wherein the RFID chip is inserted into an upper arm of the patient.

4. The method as claimed in claim 1, wherein the implant is selected from the group consisting of: an artificial permanent implant, a biological permanent implant, a temporary implant, and a medical instrument.

5. The method as claimed in claim 1, wherein a data of the patient is stored in the RFID chip.

6. The method as claimed in claim 1, wherein a location of the patient is determined by the identification data of the implant for avoiding the patient being in a vicinity of an electromagnetic field or locating a missing patient within the hospital.

7. The method as claimed in claim 1, wherein the implant is identified before performing a medial examination or treatment for not impairing the implant or a wellbeing of the patient during the medial examination or treatment.

8. The method as claimed in claim 1, wherein the RFID chip is supplied with energy generated by a radio wave of the reading unit.

9. The method as claimed in claim 1, wherein the patient is a human or an animal.

* * * * *